United States Patent [19]

Hagen et al.

[11] 4,334,100
[45] Jun. 8, 1982

[54] PRODUCTION OF ALDEHYDES

[75] Inventors: Jens Hagen, Ketsch; Klaus Bruns, Krefeld-Traar, both of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 94,275

[22] Filed: Nov. 14, 1979

[30] Foreign Application Priority Data

Nov. 16, 1978 [DE] Fed. Rep. of Germany ....... 2849742

[51] Int. Cl.$^3$ .............................................. C07C 45/50
[52] U.S. Cl. .............................. 568/444; 252/522 R; 568/445
[58] Field of Search ......................... 260/598; 568/444

[56] References Cited

U.S. PATENT DOCUMENTS

| | | | |
|---|---|---|---|
| 2,327,066 | 8/1943 | Roelen | 260/598 |
| 2,880,241 | 3/1959 | Hughes | 260/598 X |
| 3,239,566 | 3/1966 | Slaugh et al. | 260/598 X |
| 3,499,932 | 3/1970 | Pruett et al. | 260/598 |
| 4,081,477 | 3/1978 | Hoffmann et al. | 568/444 |

FOREIGN PATENT DOCUMENTS 151446 5/1953 Australia .............................. 568/444

OTHER PUBLICATIONS

Kogami et al., Yukagu, vol. 22, No. 6, (1973), 316-320.

Primary Examiner—Bernard Helfin
Attorney, Agent, or Firm—Hammond & Littell, Weissenberger and Muserlian

[57] ABSTRACT

This invention is directed to a process for preparing aldehydes by hydroformylation of monoterpene compounds, which comprises reacting a monocyclic or bicyclic monoterpene compound with at least one double bond at from about 70° to 160° C. under a pressure of from about 100 to 400 bar and in the presence of a catalyst mixture of tertiary phosphines and rhodium carbonyl complexes containing tertiary phosphines. The aldehydes prepared are useful as perfuming agents.

1 Claim, No Drawings

PRODUCTION OF ALDEHYDES

FIELD OF THE INVENTION

This invention is directed to a novel process for the production of aldehydes. More specifically, this invention is directed to a process for the production of aldehydes from monocyclic and bicyclic monoterpene hydrocarbons, as well as to the use of such aldehydes as perfumes.

BACKGROUND OF THE INVENTION

In the hydroformylation of terpenes under the conditions customary in the oxo reaction and in the presence of dicobalt octacarbonyl, complex product mixtures are formed which contain aldehydes, alcohols, acetals, ethers, and rearrangement products of the respective terpene hydrocarbons (W. H. Clement et al., *Ind. Eng. Chem. Prod. Res. Dev.*, Vol. 4 (1965), pp. 283–286). Less complicated compound mixtures have been obtained with the hydroformylation of α-pinene in the presence of rhodium catalysts (W. Himmele et al., *Tetrahydron Letters*, 1976, pp. 907–910). The reaction mixture contained in this case, in addition to the desired 3-formylpinane, a considerable proportion of the two isomeric 10-formylpinanes, which can form only if under the reaction conditions an isomerization of the double bond of the α-pinene occurs.

OBJECTS OF THE INVENTION

It is an object of the invention to provide a novel process for the production of aldehydes.

It is also an object of the invention to provide a novel process for the production of aldehydes from monocyclic and bicyclic terpenes.

It is further an object of the invention to provide for the use of the aldehydes as perfuming agents.

These and other objects of the invention will become more apparent in the discussion below.

DESCRIPTION OF THE INVENTION

It has now been surprisingly found that the isomerization of the double bonds present in the terpene hydrocarbons can, under the conditions of the hydroformylation reaction, be suppressed to a large extent if a catalyst mixture consisting of tertiary organic phosphines and rhodium carbonyl compounds is used. Therefore, according to the invention, aldehydes are produced by hydroformylation of monocyclic and bicyclic monoterpene hydrocarbons with at least one double bond, the production being characterized in that the hydroformylation is carried out at from about 70° to 160° C. under a pressure of from about 100 to 400 bar and in the presence of a catalyst mixture of tertiary phosphines and rhodium carbonyl complexes containing these tertiary phosphines.

Suitable tertiary phosphines include trialkyl phosphines wherein the alkyl radicals have from about 1 to 20 carbon atoms, as well as triphenyl phosphines wherein the phenyl radicals may be substituted by alkyl or alkoxy groups with 1 to 4 carbon atoms, triphenyl phosphine being preferred. In the catalyst mixtures the molar number of total phosphine present per gram atom of rhodium is in the range of from about 20 to 200.

The exact composition of the catalytically active rhodium carbonyl complexes is not known. Presumably, however, one or more carbonyl ligands in the complexes have been replaced by phosphine ligands.

The actual active rhodium carbonyl complex compound is formed in each case in situ under the hydroformylation conditions. The quantity of rhodium required for this purpose can be supplied to the reaction mixture in the form of suitable rhodium compounds, such as rhodium chloride, rhodium oxide, rhodium salts of fatty acids, rhodium chelates, rhodium carbonyl or dimeric rhodium carbonyl chloride, or mixtures thereof. Preferably, the rhodium complexes employed are those in which phosphine is already present in the catalyst mixture as a ligand, the compound $RhCl(CO)[P(C_6H_5)_3]_2$ being especially preferred.

Advantageously, the rhodium compounds are used in quantities based on the amount of terpene hydrocarbon present, of from about 5 to 5,000 ppm, preferably from about 15 to 400 ppm, calculated as metal.

Useful starting materials for the production of aldehydes by the process according to the invention include monocyclic and bicyclic monoterpene hydrocarbons with at least one double bond, compounds with endocyclic double bonds as well as those with semicyclic and exocyclic double bonds entering into consideration. As examples of such terpene hydrocarbons, the isomeric menthenes, β-terpinene, λ-terpinene, α-phellandrene, β-phallandrene, dipentene, pseudolimonene, terpinol and α-pinene, as well as limonene α-terpinene, β-pinene, and camphenes may be mentioned. Also, naturally occurring mixtures which contain predominantly such terpene hydrocarbons, for example, orange oil, should be considered as starting materials.

The reaction can be carried out in the absence of solvents; however, it has proven expedient to use solvents. Useful solvents include saturated hydrocarbons having from 1 to 8 carbon atoms, such as pentane, hexane, heptane, and cyclohexane; aromatics such as benzene, toluene, and xylene; cyclic ethers such as tetrahydrofuran and dioxane; alcohols such as methanol, ethanol, and isopropanol; and diols such as ethylene glycol and propylene glycol. Preferably, the hydroformylation is carried out in a saturated hydrocarbon or cyclic ether.

The reaction mixture is worked up by distillation, which is advantageously carried out in an inert gas atmosphere, such as, for example, a nitrogen atmosphere, The reaction products formed in the described hydroformylation according to the invention are, as a rule, mixtures of the possible stereoisomers of the desired aldehyde compound. These mixtures have perfume properties and can be mixed with other perfumes in various quantity ratios to form new perfume compositions. Generally the proportion of a mixture in a perfume composition will range from about 1 to 50 percent by weight, based on the weight of the total composition. Such compositions can serve directly as perfume or as perfuming agents in cosmetics, such as creams, lotions, odorizers, aerosols, toilet soaps, and the like. Also, the compositions may be used to improve the odor of technical products such as detergents and cleansing agents, softeners, textile treatment agents, and the like. To perfume the various products, the perfume compositions containing the mixtures according to the invention are added to the products generally in concentration of from about 0.05 to 2 percent by weight, based on the weight of the products.

The following Examples are intended to illustrate the invention and are not to be construed as limiting the invention thereto.

EXAMPLE 1

In a five-liter stroke agitator autoclave of stainless steel, 1360 g (10 mols) of limonene, 15.2 g (58 mmol) of triphenyl phosphine, and 0.4 g (0.58 mmol) of RhCl(CO)[P(C$_6$H$_5$)$_3$]$_2$ were mixed together. The autoclave was flushed with a synthesis gas.

Then, a mixture consisting of equal volumes of hydrogen and carbon monoxide was introduced to result in a pressure of 200 bar. The autoclave contents were heated to 125° C. with agitation, maintained at this temperature for 3 hours with continued agitation, the pressure rising to a maximum of 270 bar, and then cooled to room temperature. The crude product obtained (1660 g) was distilled in vacuum under nitrogen atmosphere. After separation of the unreacted limonene, 1381 g of 3-(4-methyl-3-cyclohexyl) butyraldehyde distilled off at 111° to 112° C. at 16 mbar. This represented 83% of theory.

The iodine number of the product was 155 (theory, 153). According to a gas chromatographic test, the product had a purity of 98%. The product showed the following IR spectrum (film): 3005 cm$^{-1}$;

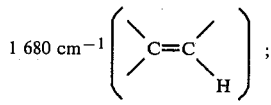

2710 cm$^{-1}$; 1726 cm$^{-1}$ (CHO).

Odor: "Agrumen" note, rhubarb note.

EXAMPLE 2

Four hundred and eight grams (3 mols) of camphene, 7.6 g (29 mmol) of triphenyl phosphine, and 0.2 g (0.29 mmol) of RhCl(CO)[P(C$_6$H$_5$)$_3$]$_2$ were mixed together in a five-liter stroke agitator autoclave. The autoclave was flushed with synthesis gas.

Then, a mixture consisting of equal volumes of hydrogen and carbon monoxide was introduced to result in a pressure of 200 bar. The autoclave contents were heated to 120° C. with agitation and maintained at from 120° to 130° C. for 4 hours with additional agitation. After cooling, the crude product obtained was processed by distillation. At 105° to 106° C., 20 mbar, 338 g of 3,3-dimethyl-2-norbornanacetaldehyde was distilled off. This represented 77% of theory.

According to a gas chromatographic analysis, 98% of the product consisted of a mixture of the endo and the exo-stereoisomers.

The product showed the following IR spectrum (film): 2710 cm$^{-1}$; 1728 cm$^{-1}$ (CHO); 1385 cm$^{-1}$; 1365 cm$^{-1}$ (mixed dimethyl).

Odor: Borneol note; campher note.

EXAMPLE 3

A five-liter stroke agitator autoclave was charged with 272 g (2 mols) of β-pinene, 7.6 g (29 mmol) of triphenyl phosphine, 0.2 g (0.29 mmol) of RhCl(CO)[P(C$_6$H$_5$)$_3$]$_2$, and 750 ml tetrahydrofuran and flushed with synthesis gas. Then, a gas mixture consisting of equal volumes of hydrogen and carbon monoxide was introduced to result in a pressure of 200 bar. The reaction mixture was heated to 130° C. with agitation and maintained at that temperature for two hours. After cooling, the crude product obtained was processed by distillation. At 105° to 107° C., 20 mbar, 222 g of 10-formylpinane was distilled off (67% of theory).

According to a gas chromatographic analysis, 97% of the product consisted of a mixture of the axial and equatorial stereoisomers.

The product showed the following IR spectrum (film): 2710 cm$^{-1}$; 1725 cm$^{-1}$ (CHO); 1368 cm$^{-1}$; 1381 cm$^{-1}$ (mixed dimethyl).

Odor: green, citronellal note, magriffe note.

EXAMPLE 4

In a five-liter stroke agitator autoclave 272 g (2 mols) of α-terpinene, 3.8 g (14.5 mmol) of P(C$_6$H$_5$)$_3$, 0.2 g (0.29 mmol) of RhCl(CO)[P(C$_6$H$_5$)$_3$]$_2$, and 750 ml of tetrahydrofuran were mixed together. The autoclave was flushed with synthesis gas.

Then, a mixture consisting of equal volumes of hydrogen and carbon monoxide was introduced to result in a pressure of 200 bar. The autoclave contents were heated with agitation to 130° C., maintained at 130° to 140° C. for five hours, and then cooled to room temperature. Tetrahydrofuran was distilled off from the reaction mixture under water jet vacuum. During distillation of the residue under oil pump vacuum, 225 g of product distilled off at 98° to 100° C. at 20 mbar. This represented 68% of theory.

A gas chromatographic analysis showed that the product constituted a mixture of 2-formyl-Δ3-menthene and 3-formyl-Δ1-menthene.

The product showed the following IR spectrum (film): 3005 cm$^{-1}$;

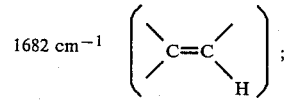

2700 cm$^{-1}$; 1725 cm$^{-1}$ (CHO); 1380 cm$^{-1}$; 1360 cm$^{-1}$ (isopropyl); 845 cm$^{-1}$ (C=C trisubstituted).

Odor: Salicylate note, cumin-perilla note.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A process for preparing aldehydes by hydroformylation of monoterpene compounds, which comprises reacting a monocyclic or bicyclic monoterpene compound selected from the group consisting of limonene, camphene, β-pinene, and α-terpinene at from about 70° to 160° under a pressure of from about 100 to 400 bar and in the presence of a catalyst mixture consisting essentially of triphenyl phosphine and RhCl(CO)[P(C$_6$H$_5$)$_3$]$_2$.

* * * * *